US00PP19056P2

(12) United States Plant Patent
Giesen

(10) Patent No.: US PP19,056 P2
(45) Date of Patent: Jul. 29, 2008

(54) ***LOBELIA* PLANT NAMED 'TECH HEUPBULE'**

(50) Latin Name: *Lobelia erinus*
Varietal Denomination: Tech Heupbule

(75) Inventor: Eric Giesen, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 11/732,453

(22) Filed: Apr. 3, 2007

(51) Int. Cl.
*A01H 5/00* (2006.01)

(52) U.S. Cl. ..... Plt./451
(58) Field of Classification Search ..... Plt./451, Plt./263
See application file for complete search history.

*Primary Examiner*—Kent L. Bell
*Assistant Examiner*—S. B. McCormick-Ewoldt
(74) *Attorney, Agent, or Firm*—Jondle & Associates, P.C.

(57) ABSTRACT

A new *Lobelia* plant particularly distinguished by its semi-upright, pendulous and compact form, vigorous plant habit, dense and free branching, short internodes, large, blue flowers and tolerance to heat is disclosed.

1 Drawing Sheet

Genus and species: *Lobelia erinus*
Variety denomination: 'Tech Heupbule'.

BACKGROUND OF THE NEW PLANT

The present invention comprises a new and distinct cultivar of *lobelia,* botanically known as *Lobelia erinus,* and hereinafter referred to by the cultivar name 'Tech Heupbule'. The new cultivar originated from a hybridization made in January 2004 in Andijk, The Netherlands. The female parent was 'LOB04-203', a blue proprietary *lobelia* line (unpatented), while the male parent was 'LOB02-14-2', a blue proprietary *lobelia* line (unpatented).

The seeds produced by the pollination were sown in March 2004. A single plant selection was chosen for further evaluation and for asexual propagation in July 2004.

The new cultivar was created in 2004 and has been asexually reproduced repeatedly by vegetative cuttings and tissue culture in Gilroy, Calif. and Andijk. The Netherlands over a two and a half year period. The plant has also been trialed at Gilroy, Calif., Andijk, The Netherlands and Hillscheid Germany. The present invention has been found to retain its distinctive characteristics through successive asexual propagations.

Plant Breeder's Rights for this cultivar have been applied for with the European Union on Nov. 13, 2006.

SUMMARY OF THE INVENTION

The following are the most outstanding and distinguishing characteristics of this new cultivar when grown under normal horticultural practices in Gilroy, Calif., and Andijk, The Netherlands.

1. Semi-upright, pendulous and compact form;
2. Vigorous plant habit;
3. Dense and free branching;
4. Short internodes;
5. Large, blue flowers; and
6. Tolerance to heat.

DESCRIPTION OF PHOTOGRAPHS

This new lobelia plant is illustrated by the accompanying photographs which show overall plant habit including blooms, buds, and foliage of the plant. The colors shown are as true as can be reasonably obtained by conventional photographic procedures.

Figure 1:
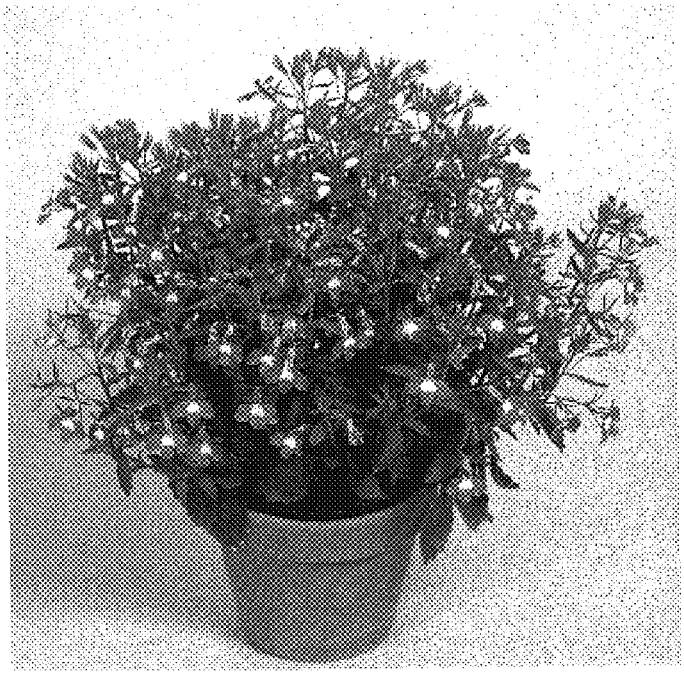

FIG. 1. shows overall plant habit including blooms, buds, and foliage of 10 to 12 weeks old plants, grown in a greenhouse in Hillscheid, Germany in May 2006.

Figure 2:
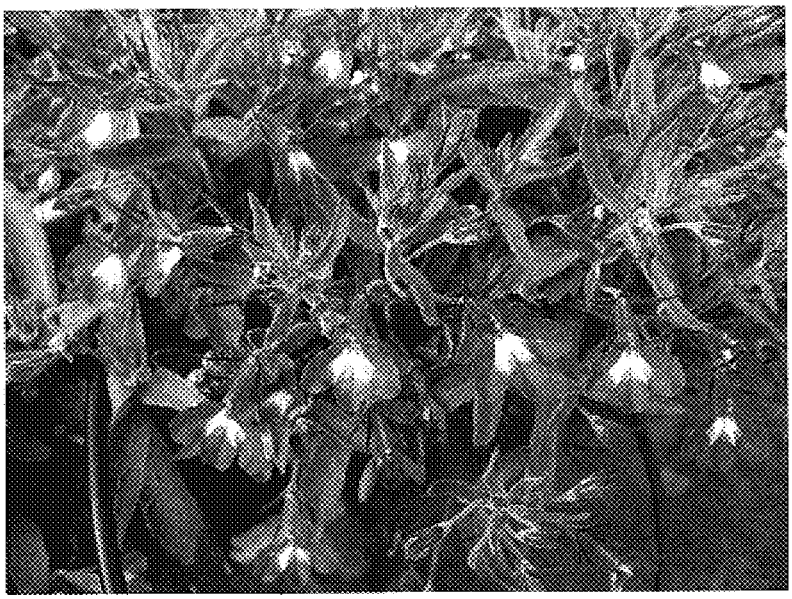

FIG. 2. shows a close-up of the blooms, buds and foliage of 10 to 12 weeks old plant in Andijk, The Netherlands in August 2005.

DESCRIPTION OF THE NEW CULTIVAR

The following detailed descriptions set forth the distinctive characteristics of 'Tech Heupbule'. The data which define these characteristics were collected in the fall and winter season from 20–22 week-old plants grown in 6-inch pots in Gilroy, Calif. The plants had one plant growth regular treatment and one terminal pinch at the onset of the trail. Color readings were taken in a greenhouse in December under natural light. Color references are primarily to the RHS Colour Chart of The Royal Horticultural Society of London (R.H.S.) (2001 edition). Texture description details were observed under a dissecting microscope.

DETAILED BOTANICAL DESCRIPTION

Classification:
*Botanical.*—*Lobelia erinus.*
*Common name.*—*Lobelia.*

Parentage:
*Female parent.*—'LOB04-203' proprietary *lobelia* line (unpatented).
*Male parent.*—'LOB02-14-2' proprietary *lobelia* line (unpatented).

Growth:
*Growth and branching habit.*—Good vigorous habit, dense and freely branched with short internodes; exhibits some heat tolerance.

*Form.*—Herbaceous annual, semi-upright and compact, pendulous.

*Height* (*measured from the top of the soil, including any flower*).—20.0 cm to 25.0 cm.

*Width* (*horizontal plant diameter, including any flower*).—40.0 cm to 50.0 cm.

*Time to produce a finished flowering plant.*—9 to 11 weeks for a 6-inch pot.

*Outdoor plant performance.*—Patio planters in mixed container plantings or garden beds.

*Time to initiate roots.*—21 to 28 days at 68 to 74 degrees Fahrenheit.

*Root description.*—Fibrous, freely-branching, and white.

Leaves:

*Arrangement.*—Alternate.

*Color.*—Immature leaf: Upper surface: RHS 137A. Lower surface: RHS 138A. Mature leaf: Upper surface: Darker than RHS 147A. Lower surface: RHS 137C.

*Length.*—4.0 cm to 4.5 cm.

*Width.*—1.1 cm to 1.6 cm.

*Shape.*—Narrow elliptical.

*Margin.*—Serrate.

*Apex.*—Broadly acute.

*Base.*—Cuneate.

*Texture.*—Pilose on both surfaces.

*Venation.*—Pinnate.

*Venation color.*—RHS 143A.

Stems:

*Length.*—25.0 cm to 30.0 cm.

*Diameter.*—0.2 cm.

*Internode length.*—1.5 cm to 2.5 cm.

*Color.*—RHS 137A.

*Texture.*—Pilose.

*Stem anthocyanin.*—Absent.

*Peduncle.*—Color: Between RHS 137A and RHS 137B. Length: 3.0 cm to 3.4 cm. Diameter: 0.1 cm. Texture: Pilose.

Flower buds:

*Shape.*—Oval to oblong.

*Diameter.*—0.3 cm to 0.4 cm.

*Length.*—1.0 cm to 1.1 cm.

*Color when bud is first starting to open.*—Base color RHS N155C with shades of RHS 96C and RHS 96D along the top and length of the bud.

Inflorescence:

*Blooming habit.*—Plants flower freely and continuously in the growing season from spring to the fall.

*Lastingness of individual blooms on plant.*—4 to 8 days depending on environmental conditions.

*Fragrance.*—None.

*Inflorescence type.*—Flowers form at apical axils, with one flower per axil; flowers are labiate; upper petal has two small lobes and lower lip has three larger and broader lobes; lobes are fused at the base.

*Quantity of flowers and buds per flowering branch.*—25 to 35.

Flowers:

*Flower diameter* (*horizontal*).—2.0 cm to 2.1 cm.

*Flower height* (*vertical*).—1.7 cm to 2.0 cm.

*Immature flower.*—Color: Upper lobe: Upper surface: Slightly darker than RHS 95B. Lower surface: RHS 97B. Lower lobe. Upper surface: RHS 95B. Lower surface: RHS 97B.

*Mature flower.*—Upper lobe: Color: Upper surface: Fading closest to RHS 96B. Lower surface: RHS 97B. Length: 0.7 cm. Width: 0.35 cm to 0.4 cm. Shape: Oblong. Apex: Abruptly acute. Margin: Entire. Texture: Upper surface: Papillose. Lower surface: Papillose; pilose. Lower lobes: Color: Upper surface: Fading between RHS 96B and RHS 96C; basal eye of RHS N155D but whiter; Lower surface: RHS 97B. Length: 1.0 cm to 1.1 cm. Width: 0.8 cm. Shape: Oblong to oblanceolate. Apex: Mucronulate. Margin: Entire. Texture: Upper surface: Papillose. Lower surface: Papillose; pilose.

*Corolla.*—Color: Inside: Closest to RHS N155A but whiter; some areas have slight shades of RHS 97C; 2 basal bars of RHS 144A. Outside: Upper portion is RHS 96D. Tube length: 1.1 cm to 1.3 cm. Diameter: 0.4 cm to 0.5 cm at the throat; 0.2 to 0.25 at the base.

*Calyx.*—Five sepals with fused bases that curve out and away from the corolla. Color: Upper surface: RHS 137A. Lower surface: RHS 137B. Length: 1.1 cm to 1.2 cm. Diameter: 0.15 cm to 0.2 cm. Shape: Linear. Apex: Acuminate. Texture: Pilose mainly on the margins and midvein.

Reproductive organs:

*Androecium.*—Number of anthers: 5 fused around the stigma. Filament length: 0.7 cm. Filament color: RHS N155D but whiter. Pollen color: RHS 4C. Pollen amount: Moderate.

*Gynoecium.*—Pistil length: 1.0 cm. Stigma color: RHS N82C. Style color: RHS 144C. Style length: 0.7 cm to 0.8 cm.

Fruit and seed set: Has not been observed.

Disease and insect resistance: Resistance and susceptibility is typical of the species.

COMPARISON WITH KNOWN CULTIVARS

'Tech Heupbule' differs from the female parent, 'LOB04-203', proprietary breeding line (unpatented), in that 'Tech Heupbule' has more and larger foliage. 'Tech Heupbule' has shorter and thicker stems than 'LOB04-203'. Additionally, 'Tech Heupbule' has larger flowers.

'Tech Heupbule' differs from the male parent, 'LOB02-14-2', proprietary breeding line (unpatented), in that 'Tech Heupbule' has a larger, darker blue flower than 'LOB02-14-2'. Additionally, 'Tech Heupbule' has shorter and broader leaves with a more upright plant habit than 'LOB02-14-02'.

'Tech Heupbule' differs from the commercial variety 'Balobwablu' (U.S. Plant Pat. No. 16,524) in that 'Tech Heupbule' has a larger plant habit with larger and lighter colored peduncles than 'Balobwablu'. 'Tech Heupbule' has a darker stigma than 'Balobwablu'. Additionally, 'Tech Heupbule' has flowers that start out darker but may fade more than 'Balobwablu'.

I claim:

1. A new and distinct *Lobelia* plant as shown and described herein.

* * * * *